US007393685B1

(12) United States Patent
Jordan

(10) Patent No.: US 7,393,685 B1
(45) Date of Patent: Jul. 1, 2008

(54) METHOD FOR CULTIVATING CANCER CELLS FROM HUMAN TISSUE AND DEVICE FOR PREPARING TISSUE SAMPLES

(75) Inventor: Andreas Jordan, Berlin (DE)

(73) Assignee: MagForce Applications GmbH, Berlin (DE)

( * ) Notice: Subject to any disclaimer, the term of this patent is extended or adjusted under 35 U.S.C. 154(b) by 0 days.

(21) Appl. No.: 09/914,662

(22) PCT Filed: Feb. 18, 2000

(86) PCT No.: PCT/DE00/00528

§ 371 (c)(1),
(2), (4) Date: Jan. 11, 2002

(87) PCT Pub. No.: WO00/53728

PCT Pub. Date: Sep. 14, 2000

(30) Foreign Application Priority Data

Mar. 10, 1999 (DE) ................................ 199 12 798

(51) Int. Cl.
*C12N 5/08* (2006.01)
*G01N 33/52* (2006.01)

(52) U.S. Cl. .................... 435/373; 435/374; 435/378; 435/379; 435/408; 436/64

(58) Field of Classification Search ................ 435/379, 435/385, 387, 392, 402, 405, 373, 374, 378, 435/408
See application file for complete search history.

(56) References Cited

U.S. PATENT DOCUMENTS 5,985,290 A 11/1999 Jaffee et al.
6,376,169 B1 * 4/2002 Adams et al. .................. 435/4

FOREIGN PATENT DOCUMENTS

DE 4334281 4/1995
DE 19912798 2/2000
WO WO91/17240 * 11/1991
WO 9524464 9/1995
WO 9723602 7/1997
WO WO 98/02038 * 1/1998

OTHER PUBLICATIONS

Trent (In: In Vitro Methods of Cancer Research, vol. III, pp. 153-187, CRC Press, Mukta Webber, Ed. 1986).*
Freshney, Culture of Animal Cells, 3rd Ed., 1994, pp. 264 and pp. 84-100.*
Abstract of Joyce et al (Pathology, 1985, vol. 17, pp. 355-359).*
Freshney (Culture of Animals Cells, 3rd Ed., 1994, pp. 79 and 101-102).*
Abstract of Ogden et al (Journal of Oral Pathology and Medicine, 1992, vol. 21, pp. 17-20).*
Abstract of Ellis et al (journal of Respiratory and Critical Care Medicine, 1994, vol. 149, pp. 118-122).*
Abstract of Jeng et al (Journal of Surgical Research, 1996, vol. 61, pp. 477-481).*
Freshney, Culture of Animal Cells, 1994, p. 350-351.*
Freshney, "Culture of Animal Cells", 1994, p. 88.*

* cited by examiner

*Primary Examiner*—Karen A. Canella
(74) *Attorney, Agent, or Firm*—Wood, Phillips, Katz, Clark & Mortimer

(57) ABSTRACT

The invention relates to a method for cultivating cancer cells for scientific serial assays, wherein a tissue sample which is heterogeneous with respect to contaminants, normal cells and tumor cells is locally separated in a sequential-parallel splitting method. The locally separated sample segments are further split, wherein the tissue fragments and liquids of the tissue segments are separately placed in a given cell culture medium and grown under predetermined culture conditions. The invention also relates to a cell culture medium and a device for splitting the tissue samples into disc segments. The inventive method combined with the splitting device and the culture medium enables fast cultivation of cancer cells obtained from human tissue with a multiplication rate of 100% in all types of tumors.

5 Claims, 2 Drawing Sheets

METHOD FOR CULTIVATING CANCER CELLS FROM HUMAN TISSUE AND DEVICE FOR PREPARING TISSUE SAMPLES

This invention relates to a method for cultivating cancer cells from human tissue for scientific, most preferably molecular-biological and cytobiological mass screenings, as well as a cell culture medium for performing this method and an apparatus for preparing the tissue samples.

Cultivation of primary cell material obtained from fine needle and punch biopsies is of vital importance for molecular biological screenings, particularly when performed with a predictive intention. However, the "successful growth" rate of cells isolated from human tissue is very low with the known methods. And for some types of tumors, cell cultivation has failed altogether. One reason for this problem is the fact that the normal cells surrounding the tumor tissue and/or connective tissue cells that infiltrate the tumor tissue are the first to grow and thus may grow over the tumor cells to be isolated for the experiments and prevent their growth. In addition, successful cultivation of cancer cells is prevented by manifold contaminants, in particular, with bacteria or fungi.

Media that have been used for cultivating tumor cells such as RPMI 1640, Basal Medium Eagle, ISCOVE's, Medium 199, Leibovitz L-15, etc. are incapable of appropriately enhancing cancer cell growth while preventing the growth of normal cells and bacterial contaminants. The common uncontrolled application of antibiotics counteracts these adverse influences but also limits the growth of the tumor cells.

According to the known methods of cultivating cancer cells, the tissue samples obtained by fine needle or punch biopsies are prepared using mechanical and enzymatic tissue disintegration in which the heterogeneous and multi-layered contents of the punching cylinder is finely ground into a pulpy mass and converted into individual cells using enzymes. But this fine grinding destroys the heterogeneous structure of the tissue sample taken, and tumor cells are intensely intermixed with normal cells and contaminants. On the one hand, fine grinding impairs the viability of the tumor cells. On the other hand, destruction of the heterogeneity of the tissue sample mixes the sample material pulp with normal cells and contaminants, and growth of the tumor cells is reduced or even prevented for the reasons mentioned above. This type of mechanical and enzymatic disaggregation of the entire material does not allow any statements on the structure of the tumor.

According to known methods of multiplying and purifying the tumor material obtained from a sample tissue, cells are multiplied by transplanting the tumor material onto a nude mouse (xenotransplantate). This method may result in successful growth rates of 50% or sometimes even more for the transplanted tumor tissue, but, depending on the tumor type and properties, it takes several weeks or even months before in-vivo cell proliferation begins. The tremendous effort involved and the long time required for growth have prevented routine tests with patient-specific primary cells from becoming standard clinical practice for progress checks and predictive purposes. As the cultivation of tissue taken from a patient is tedious and may fail, test results, if any, become available much too late for a timely change of therapy based on a routine testing procedure. Disadvantages in addition to the long time the tests take are the required animal experiments and high expenses.

It is therefore the problem of this invention to provide a method for cultivating cancer cells from human tissue samples that does not depend on laboratory animals, ensures proliferation of tumor cells from a tissue sample in a comparatively short period of a few days and facilitates reproducible statements on the structure and malignity of a tumor and on changes in growth or structure or therapeutic effects. Another problem of this invention is to provide an apparatus based on such method for reproducible preparation of tissue samples and a suitable medium for in-vitro proliferation of cancer cells.

This problem is solved according to the invention by a method for cultivating cancer cells that has the characteristics specified in claim 1.

The general concept of the invention is to split the tissue sample in a sequential and parallel cutting process into multiple individual tissue segments, thereby locally separating the heterogeneous nature of the tissue sample, i.e. its composition of contaminants, normal cells, and tumor cells. Each tissue segment is then ground separately, and the small separated tissue fragments and fluids formed in this way, as well as the tissue fluid obtained separately during sequential and parallel splitting of the tissue sample, are cultivated in a specific medium under selected cultivation conditions. This local separation of the tissue sample eliminates or reduces any influences of normal cells contained in it which, in the conventional mechanical and enzymatic preparation of the tissue sample, may overgrow the tumor cells. The amount of contaminants such as fungi or bacteria is considerably reduced, and antibiotics that are known to interfere with tumor cell proliferation can be used in a more sparing and concerted way without having an adverse effect on cancer cell cultivation.

The proposed method is advantageously supplemented for the further perfection of the invention by a medium suitable for very small amounts of tissue composed of inorganic salts, specifically: $Ca(NO_3)_2$ 10-100 mg/L, $CaCl_2\text{-}H_2O$ 80-150 mg/L, KCl 200-1000 mg/L, $MgSO_4 7H_2O$ 200-700 mg/l, NaCl 300-10000 mg/L, $NaHCO_3$ 1500-4000 mg/L, $Na_2HPO_4$ 100-1000; amino acids, specifically: L-Arginine-4HCl 10-500 mg/L, L-Asparagine (free base) 10-500 mg/L, L-Glutamine 10-500 mg/L, Glycine 10-500 mg/L, L-Histidine (free base) 10-500 mg/L, L-Hydroxyproline 10-500 mg/L, L-Isoleucine 10-500 mg/L, L-Leucine 10-500 mg/L, L-Lysine-HCL 10-500 mg/L, L-Methioninc 10-500 mg/L, L-Phenylalanine 10-500 mg/L, L-Proline 10-500 mg/L, L-Serine 10-500 mg/L, L-Threonine 10-500 mg/L, L-Tryptophane 5-400 mg/L, L-Tyrosine 10-500 mg/L, L-Valine 10-500 mg/L, L-Alanine 10-300 mg/L; vitamins, specifically: Biotin 0,01-10 mg/L, D-Ca-Pantothenate 0,01-10 mg/L, Choline Chloride 0,1-50 mg/L, Folic Acid 0,01-10 mg/L, $i$-Inositol 0,1-100 mg/L, Niacin Amide 0,01-10 mg/L, Pyridoxine-HCl 0,01-10 mg/L, Riboflavin 0,1-100 ug/L, Thiamine HCl 0,1-50 mg/L, Para-Aminobenzoic Acid 1-1000 ug/L, Vitamin B12 1-1000 ug/L, Niacin 1-100 ug/L, Ascorbic Acid 15000 ug/L, Folinic Acid 1-100 ug/L, Liponic Acid 1-100 ug/l, Vitamin A (Acetate) 10-1000 ug/L, Pyridoxine-Hcl 1-100 ug/L, Niacinamide 1-100 ug/L, α-Tocopherol phosphate 0-1000 ug/L; and D-Glucose 100-5000 mg/L, Phenol Red 0,1-1000 mg/L, Glutathione (reduced) 0,01-10 mg/L, Na-Pyruvate 0,1-50 nM, Epidermal Growth Factor (EGF), recombinant 1-3000 ng/L, Fetal Bovine Serum (FBS), Bovine Insulin (Lyophilisate) 0,1-50 mg/L and antibiotics, and by cultivation conditions such as a 0.01% to 3% oxygen atmosphere, an 0.1% to 5% carbon dioxide atmosphere, at a humidity of 100% and temperature in the range from 30 degrees C. to 36.5 degrees C.

Other advantageous characteristics of this method are disclosed in the subordinate claims. For example, it was found that the tumor cells grow particularly fast in the presence of erythrocytes that come directly from where the tissue sample was collected from the patient and thus have a higher "successful growth" rate than cells that are allowed to grow in a pure medium. Moreover, it has proven beneficial to store the tissue sample for a minimum of 2 hours but no longer than 24 hours in a medium at a temperature in the range from 4° C. to 12° C. to adapt it to the culture medium in which the cancer cells are to be proliferated later on. Under the process conditions mentioned above, tumor cells from the prepared tissue fragments were observed to adhere to a biomatrix in the cultivation bottle as early as after 1 to 12 hours if a culture temperature similar to that of the tissue collection site is set.

Using the method of the invention which is described in greater detail with reference to an embodiment below, tumor cells can be grown in vitro in a relatively short period of time, and the cultivation of cells obtained from human tissue has a "successful growth" rate of 100%. Compared to cell proliferation achieved in the nude mouse (xenotransplantate) that showed successful growth rates of around 50%, the method of the invention does not only prevent animal experiments and save costs but also dramatically reduces the time required for reproducing the cell material from a period of several weeks or even months for in vivo tumor growth down to typically 1 to 10 days.

Thus for the first time it becomes possible to carry out fast and cost-efficient routine examinations to check the progress of cancerous diseases and for predictive purposes (radiosensitivity tests or testing sensitivity to chemotherapy or hyperthermia treatment) or for early detection of resistance to identifying new anticancer agents, to complement cytological or histopathological findings, and for fundamental research in a simple and reproducible way.

According to yet another characteristic of the invention, an apparatus for preparing the tissue sample of the invention is provided as a decisive prerequisite for successful cell proliferation. This apparatus consists of a cutting unit for sequential and parallel splitting of the tissue sample and a grinding unit for the further preparation of the tissue segments produced by the cutting component. The cutting processes performed in these units keep the respective tissue pieces and fluids coming from various parts of the heterogeneous tissue sample separated in the apparatus so that these can be selectively used for cell proliferation.

The cutting unit basically comprises a collecting pan divided into chambers with a cutting plate mounted flexibly on its top, and a cutting blade frame. Cutting grooves provided in the cutting plate at a defined spacing are open towards the collecting pan and each located on top of a chamber. The cutting blade frame includes cutting knives or wires at a spacing that corresponds to the spacing between the cutting grooves. When the tissue sample that lies on the cutting plate is cut in the area of a cutting groove, the tissue segments are smoothly separated while residual pieces and fluids are collected in the chamber below the cutting groove.

A grinding unit is provided for further preparation of the tissue segments that consists of a fluid-collecting pan divided into chambers, a preparation plate with cavities to hold tissue segments that is detachably mounted on top of said pan, and rotatory plungers that are individually mounted or mounted to a base plate on which they can be rotated and moved in longitudinal direction, said rotatory plungers comprising knives at their front sides. This unit is used to produce the small tissue fragments that are finally used for cell cultivation. The tissue fluid that results from cutting can also be used for cell cultivation; it runs through holes in the cavities into the chamber of the fluid-collecting pan located under the respective cavity.

Other characteristics and advantageous improvements of the apparatus according to the invention are disclosed in the remaining subordinate claims.

An embodiment of the invention is described below; reference will be made, in particular, to the enclosed table on in-vitro cell proliferation that shows the composition of the medium used, and to the enclosed figure as regards the preparation of the tissue samples. The figures show the following:

Figure 1:
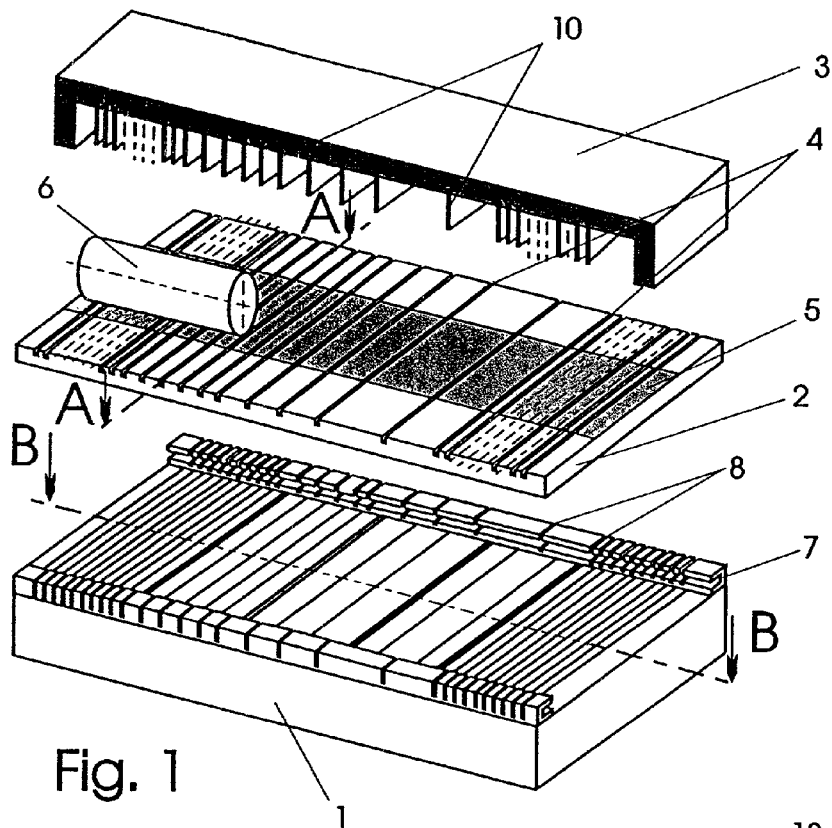
FIG. 1 is an exploded perspective view of a cutting unit for sequential and parallel preparation according to the invention of a tissue sample.

The tissue sample obtained from a patient as a fine needle or punch biopsy is available in the form of a punch cylinder but may also be a small tissue fragment or tissue piece of different shape and size obtained using another procedure. The tissue sample with erythrocytes from the collection site of the sample in the patient adhering to it is stored in a culture medium for being taken to the examination site for a minimum of 2 hours and a maximum of 24 hours at temperatures in the range from 2° C. to 12° C. Mechanical strain on the tissue piece should be avoided in this period. The tissue sample can be adapted to the culture medium that is later to be used for cultivation, for which the temperatures specified are most favorable.

The tissue sample is prepared for cell cultivation using the units shown in the figures.

The apparatus for sequential and parallel splitting of the tissue sample into segments of a specified length and for separating these segments from each other or from their ingredients comprises a collecting pan 1, a cutting plate 2 mounted to the collecting pan 1, and a cutting blade frame 3. The cutting plate 2 is divided into five sections of equal size. Each section contains cutting grooves 4 at a different spacing, and the central part of all cutting grooves is open towards the collecting pan 1. The spacing between the cutting grooves 4 in the five sections is 1 mm, 2 mm, 3 mm, 5 mm, and 1 mm. The center section of the cutting plate comprises in its longitudinal direction a roughened support area 5 to fix the tissue sample 6 that is put on it during the cutting process. This is the area in which the cutting grooves 4 are open at their bottom sides. The cutting plate 2 can be moved along two guide rails 7 attached to the side walls of the collecting pan 1. The cutting grooves 4 in the cutting plate 2 are continued by the recesses 8 in the guide rails.

The collecting pan 1 is divided by partition walls 12 into five chambers 1a to 1e that correspond to the groove sections provided in the cutting plate 2, and more partition walls in the chambers 1a, 1b, 1c, and 1e ensure that sub-chambers 1a1 through 1a9, 1b1 through 1b4, 1c1 through 1c3, and 1e1 through 1e9 are assigned to the cutting grooves. These sub-chambers are marked for exact allocation of each tissue sample segment 6a or tissue sample residue or fluid.

The cutting blade frame 3 consists of a lid or holding frame with cutting blades 10 mounted to its top panel. Cutting wires may stretch from one side of the frame to the other as an alternative to the cutting blades 10. The cutting blades 10 are placed at the same spacing as the cutting grooves 4 in the cutting plate. The cutting blade frame 3 is configured, or the cutting blades are arranged, so that the cutting elements can be moved back and forth via or in the cutting grooves 4 and the recesses 8. The cutting blade frame 3 may be hinged to a side wall of the collecting pan in such a way that it can still be moved in transverse direction to the tissue sample when positioned on the cutting plate 2 to provide smooth cutting edges for the sample segments.

The tissue sample 6 is placed on the roughened support surface 5 of the cutting plate 2 depending on the length of the tissue sample and the required spacing of the cuts. The preparation is cut at the cutting grooves 4 by moving the cutting blade frame 3 back and forth after putting (flapping) it onto tissue sample. Any fluid resulting from the cutting process runs from the support surface 5 of the cutting plate 2 via the holes 4a provided in the cutting grooves 4 into the sub-chamber that lies beneath. The fluid collected may be used for cell cultivation as well as the sample segments that either remain on the cutting plate 2 or drop through the hole 4a in the cutting groove 4 into the sub-chamber located underneath.

Figure 3:
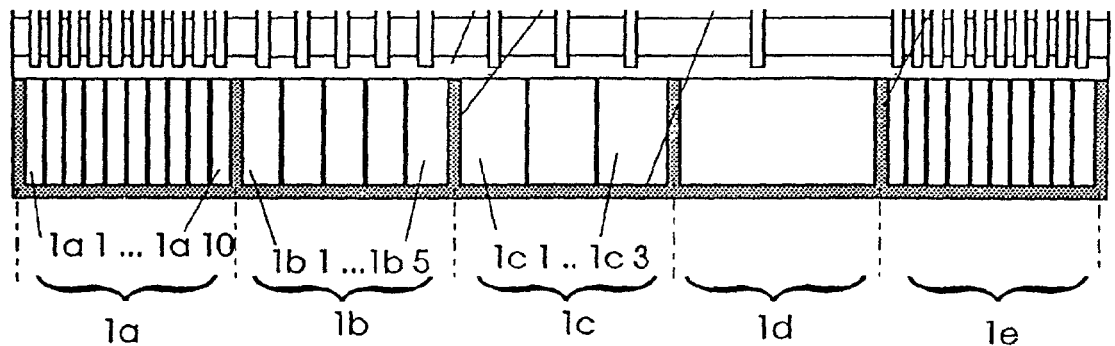
FIG. 3 is a cross-sectional view of a collecting pan along line B-B in FIG. 1.
Figure 4:
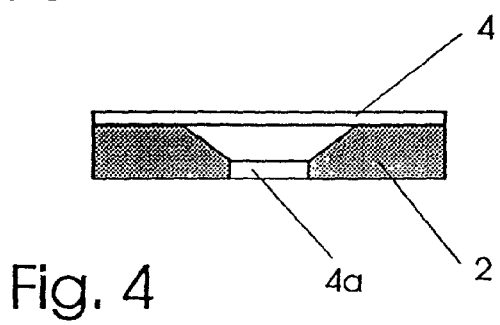
FIG. 4 is a vertical section through a cutting plate to expose a cutting groove along line A-A in FIG. 1.

The apparatus described as shown in FIGS. 1, 3, and 4 is capable of making precise, even, smooth and reproducible cuts to the specified dimensions without damaging the sample material. Thus cells are cultivated from a locally segmented tissue sample whose heterogeneity matches the tissue sample taken from the patient. This reduces or eliminates the interference of normal cells and contaminants with the growth of the tumor cells (selection). In addition, the locally separated fluid from cutting the tissue sample contains important stem cells and may be used for cell cultivation. As a result of in-vitro cell proliferation following the further preparation of the tissue sample as described below, statements can be made on the structure of the heterogeneous tissue sample, the arrangement of the tumor core, or on malignancy. Finally the type of local separation of the sample can be reproduced, which allows reliable statements on the progress of the disease or the effect of therapeutic measures.

In one embodiment of the cutting unit described above, the tissue sample can be cut using a separate cutter die (not shown) to which knives or cutting wires are mounted in a spacing that matches that of the cutting grooves 4.

Figure 2:
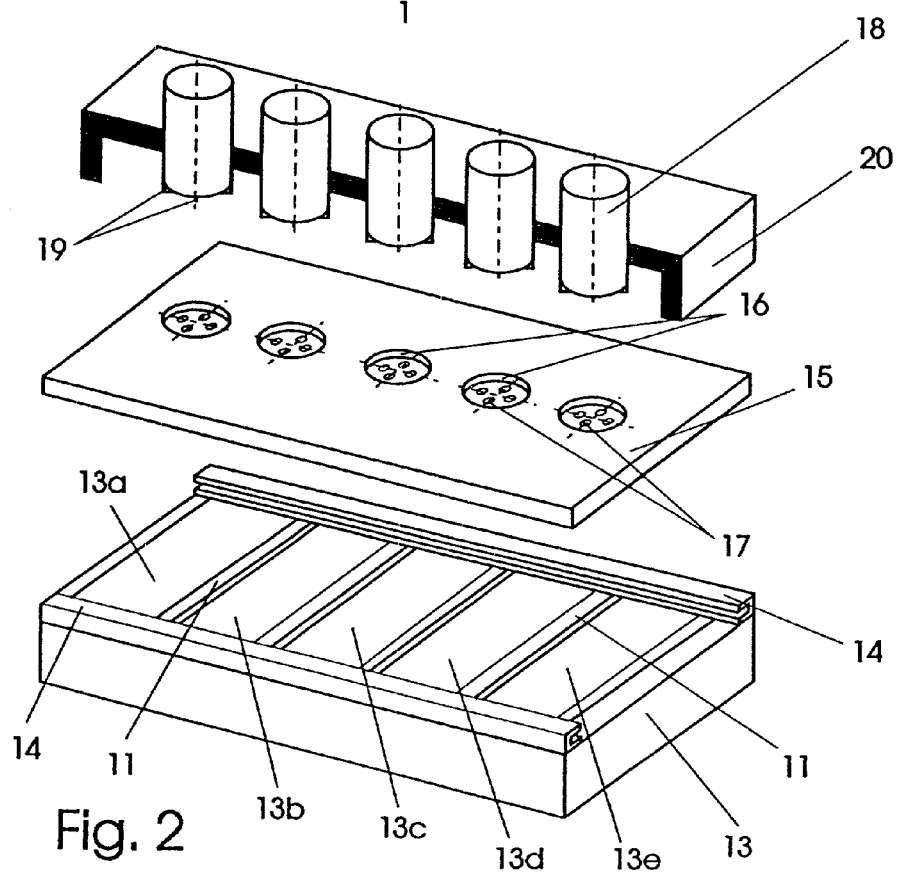
FIG. 2 is an exploded perspective view of a unit for further preparation of the tissue segments for in-vitro cell cultivation produced in the unit shown in FIG. 1.
Figure 5:
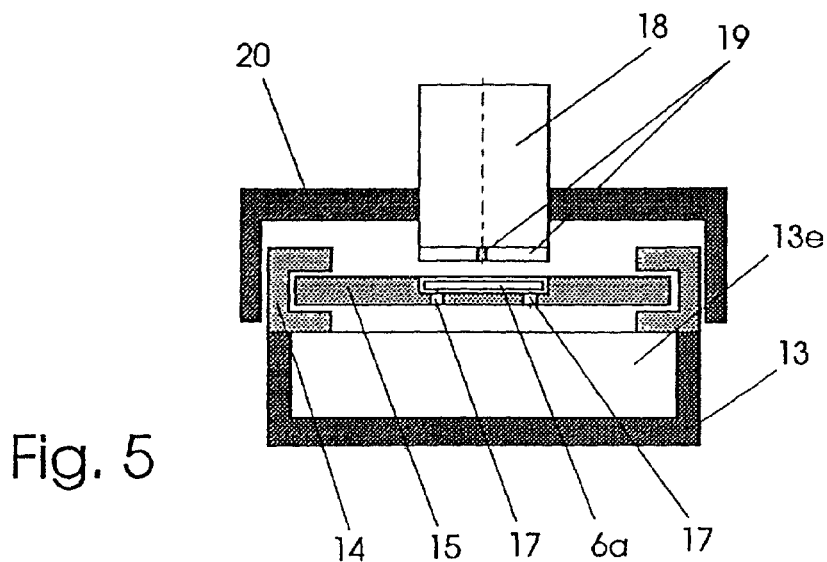
FIG. 5 is a cross-sectional view of the apparatus shown in FIG. 2 in fully assembled condition.

FIGS. 2 and 5 shows an apparatus for further preparation of the locally separated sample segments 6a or residual pieces. This unit comprises a fluid-collecting pan 13 that is divided into multiple chambers 13a to 13e using vertical partition walls 11. A preparation plate 15 with spaced recesses 16 molded into it is held by two guide rails 14 that are mounted to the upper edge of the fluid-collecting pan 13. These recesses 16 comprise small holes 17 at their bottoms. When the preparation plate 15 is completely slid into the guide rails 14, each of said recesses 16 is positioned above a chamber 13a to 13e. The separated sample segments 6a of the tissue sample 6 are put into the recesses 16 and further ground using a plunger knife 19 that is attached to a rotatory plunger 18. The front side of a rotatory plunger is preferably equipped with two or more plunger knives 19. The sample segments 6a are ground by applying a slight pressure and by turning the rotatory plunger 18 back and forth.

As FIG. 2 shows, multiple rotatory plungers 18 may be mounted to a base plate 20 on which they can be rotated, elevated, and lowered. The spacing between the rotatory plungers 18 matches the spacing between the recesses 16 in the preparation plate 15.

After the sample segments 6a have been split up more, its parts (tissue fragments) and the tissue fluid that results from cutting and runs through the holes 17 in the recesses 16 into chambers 13a to 13e are available for cell cultivation.

The apparatuses shown in FIGS. 1 through 5 for locally separated, sequential and parallel cutting and further preparation of a tissue sample are made of a material that is heat-resistant up to 121° C. and suited for autoclaving, preferably teflon, metal, or plastic. The cutting blades are preferably made of glass.

Each fragment and the respective tissue fluid of the locally separated sample segments 6a are now filled separately into cell culture bottles that contain the same medium in which the sample tissue 6 taken from the patient was stored. The remaining medium in which the tissue sample was stored after sample-taking is also filled into a culture bottle. Each cell culture bottle is coated with a biomatrix, in this example made of collagen and polylysine. The composition of the medium used for in-vitro cell cultivation is listed in the table below:

| | |
|---|---|
| Inorganic salts | |
| $Ca(NO_3)_2$ | 50 mg/L |
| $CaCl_2 \cdot 2H_2O$ | 132 mg/L |
| Kcl | 400 mg/L |
| $MgSO_4 \cdot 7H_2O$ | 150 mg/L |
| NaCl | 6400 mg/L |
| $NaHCO_3$ | 2100 mg/L |
| $Na_2HPO_4$ | 400 mg/L |
| Amino acids | |
| L-arginine•4HCl | 110 mg/L |
| L-asparagine (free base) | 38 mg/L |
| L-aspartic acid | 23 mg/L |
| L-cystine | 31 mg/L |
| L-glutamic acid | 25 mg/L |
| L-glutamine | 296 mg/L |
| Glycine | 13 mg/L |
| L-histidine (free base) | 12 mg/L |
| L-hydroxyproline | 10 mg/L |
| L-isoleucine | 38 mg/L |
| L-leucine | 38 mg/L |
| L-lysine•HCl | 35 mg/L |
| L-methionine | 12 mg/L |
| L-phenylalanine | 16 mg/L |
| L-proline | 22 mg/L |
| L-serine | 26 mg/L |
| L-threonine | 22 mg/L |
| L-tryptophane | 5 mg/L |
| L-tyrosine | 19 mg/L |
| L-valine | 22 mg/L |
| L-alanine | 10 mg/L |
| Vitamins | |
| Biotin | 0.6 mg/L |
| D-Ca-pantothenate | 0.7 mg/L |
| Choline chloride | 3.5 mg/L |
| Folic acid | 1.0 mg/L |
| i-Inositol | 35.9 mg/L |
| Niacin amide | 1.0 mg/L |
| Pyridoxine•HCl | 1.0 mg/L |
| Riboflavin | 20 µg/L |
| Thiamine•HCl | 1.0 mg/L |
| Paraminobenzoic acid | 500 µg/L |
| Vitamin $B_{12}$ | 5 µg/L |
| Niacin | 25 µg/L |
| Ascorbic acid | 50 µg/L |
| Folinic acid | 6 µg/L |
| Liponic acid | 21 µg/L |
| Vitamin A (acetate) | 100 µg/L |
| Pyridoxine•HCl | 25 µg/L |
| Niacinamide | 25 µg/L |
| α-Tocopherol phosphate | 10 µg/L |
| Other components | |
| D-glucose | 1750 mg/L |
| Phenol red | 7 mg/L |
| Glutathione (reduced) | 0.5 mg/L |
| Sodium pyruvate | 1 mM |

-continued

| | |
|---|---|
| Epidermal growth factor (EGF) (Epidermal Growth Factor, EGF recombining | 250 ng/L |
| Fetal bovine serum (FBS) 12.5% Bovine insulin (lyophilisate) | 8 mg/L (26 U/mg) |

State-of-the-art Antibiotics

The cell culture bottles with their biomatrix substrate, containing the medium of the invention and the small tissue fragments or tissue fluid prepared as described above, are put into an incubator and stored therein at a temperature in the range from 30° C. to 36.5° C., an 0.01% to 3% oxygen atmosphere, an 0.1% to 5% carbon dioxide atmosphere, and a humidity of 100%. The exact temperature depends on the temperature that was measured when the tissue sample was taken.

The tumor cells adhere to the biomatrix substrate in the cell culture bottle as early as after 1 to 12 hours. The medium in the bottles is replaced by a fresh medium of the same composition about 24 hours after the initial establishment of the culture and after cell adhesion has started. Depending on whether contaminants are present or not, other media changes will have to be performed in the first week. When the tumor cells are established after a period of rest and start proliferating, they are kept in a medium that is free of antibiotics. Then mass proliferation is initiated.

The probability of contamination and mass proliferation of contaminants in the culture bottles is very low due to the early splitting up of the tissue sample into separate tissue segments or even smaller tissue fragments after 2 to 24 hours as described above. The few bottles that are found to have a high level of contamination are rejected. Magnetic separation may be performed if, as a result of handling errors, normal cells should proliferate strongly and overgrow the tumor cells; under the conditions specified above, selective growth of the malignant cells should be guaranteed.

LIST OF REFERENCE SYMBOLS

1 Collecting pan
1a1 through 1a10 Sub-chambers
1b1 through 1b5 Sub-chambers
1c1 through 1c3 Sub-chambers
1d
1e1 through 1e10 Sub-chambers
2 Cutting plate
3 Cutting blade frame
4 Cutting grooves
4a Hole in 4
5 Support surface
6 Tissue sample
6a Sample segment
7 Guide rail
8 Recesses
10 Cutting knives/wires
11 Partition
12 Partition
13 Fluid-collecting pan
13a through 13e Chambers
14 Guide rails
15 Preparation plate
16 Recesses
17 Holes
18 Rotatory plunger
19 Plunger knife
20 Plunger base plate

We claim:

1. A method of cultivating cancer cells from human tissue for molecular-biological mass screenings wherein a tissue sample is locally separated into disk segments by sequential and parallel mechanical splitting based on its heterogeneous structure of tumor cells, normal cells, and contaminants, and wherein said separated tissue sample segments are further split into tissue fragments, and wherein said separated tissue fragments and fluids of the locally separated tissue sample segments are selectively cultivated in a specific culture medium for cultivating tumor cells and under predefined cultivation conditions and under suppression of the disturbing influence or normal cells and contaminants, and wherein the tissue fragments and fluids obtained from the locally separated tissue sample segments are cultivated separately in cell culture bottles filled with said culture medium for cultivating tumor cells and coated with a biomatrix substrate in an 0.01% to 3% oxygen atmosphere, an 0.1% to 5% carbon dioxide atmosphere, at a humidity of 100% and temperatures in the range from 30° C. to 36.5° C. and wherein said tissue sample is temporarily placed in a culture medium for storage together with adhering erythrocytes from the collection site of the sample in the respective patient until the tissue sample fragments are produced, and wherein the tissue sample is kept in the culture medium for storage for a minimum of 2 hours but no longer than 24 hours at temperature in the range from 4° C. to 12° C. to get adapted to said culture medium for storage, and wherein the culture medium for cultivating tumors is composed of inorganic salts, specifically

| | |
|---|---|
| $Ca(NO_3)_2$ | 50 mg/L |
| $CaCl_2 \cdot 2H_2O$ | 132 mg/L |
| KCl | 400 mg/L |
| $MgSO_4 \cdot 7H_2O$ | 150 mg/L |
| NaCl | 6400 mg/L |
| $NaHCO_3$ | 2100 mg/L |
| $Na_2HPO_4$ | 400 mg/L; |
| amino acids, specifically | |
| L-arginine•4HCl | 110 mg/L |
| L-asparagine (free base) | 38 mg/L |
| L-aspartic acid | 23 mg/L |
| L-cystine | 31 mg/L |
| L-glutamic acid | 25 mg/L |
| L-glutamine | 296 mg/L |
| Glycine | 13 mg/L |
| L-histidine (free base) | 12 mg/L |
| L-hydroxyproline | 10 mg/L |
| L-isoleucine | 38 mg/L |
| L-leucine | 38 mg/L |
| L-lysine HCl | 35 mg/L |
| L-methionine | 12 mg/L |
| L-phenylalanine | 16 mg/L |
| L-proline | 22 mg/L |
| L-serine | 26 mg/L |
| L-threonine | 22 mg/L |
| L-tryptophane | 5 mg/L |
| L-tyrosine | 19 mg/L |
| L-valine | 22 mg/L |
| L-alanine | 10 mg/L |
| vitamins, specifically | |
| Biotin | 0.6 mg/L |
| D-Ca-pantothenate | 0.7 mg/L |
| Choline chloride | 3.5 mg/L |
| Folic acid | 1.0 mg/L |
| i-Inositol | 35.9 mg/L |

-continued

| | |
|---|---|
| Niacin amide | 1.0 mg/L |
| Pyridoxine•HCl | 1.0 mg/L |
| Riboflavin | 20 mg/L |
| Thiamine•HCl | 1.0 mg/L |
| Paraminobenzoic acid | 500 mg/L |
| Vitamin $B_{12}$ | 5 mg/L |
| Niacin | 25 mg/L |
| Ascorbic acid | 50 mg/L |
| Folinic acid | 6 mg/L |
| Liponic acid | 21 mg/L |
| Vitamin A (acetate) | 100 mg/L |
| Pyridoxine•HCl | 25 mg/L |
| Niacinamide | 25 mg/L |
| a-Tocopherol phosphate and | 10 mg/L |
| D-glucose | 1750 mg/L |
| Phenol red | 7 mg/L |
| Glutathione (reduced) | 0.5 mg/L |
| Sodium pyruvate | 1 nM |
| Epidermal growth factor (EGF) | 250 ng/L |

-continued

| | |
|---|---|
| Fetal bovine serum (FBS) 12.5% Bovine insulin (lyophilisate and antibiotics. | 8 mg/L |

2. The method according to claim 1 wherein said tissue sample is obtained from fine needle, aspiration, intraoperative biopsies or a resection sample.

3. The method according to claim 1, wherein the culture medium for storage of the freshly taken sample and the culture medium for cultivating tumor cells are identical.

4. The method according to claim 1 wherein the medium in the culture bottle is replaced by a fresh medium of the same composition some time after initial establishment of the cell culture and completed adhesion.

5. The method according to claim 4 wherein the medium is replaced depending on the presence of contaminants such as bacteria and fungi, containing either the same or a reduced portion of antibiotics.

\* \* \* \* \*